United States Patent [19]

Salbaum et al.

[11] Patent Number: 5,853,985
[45] Date of Patent: Dec. 29, 1998

[54] PROMOTER OF THE GENE FOR THE HUMAN PRECURSOR OF THE ALZHEIMER'S DISEASE AND ITS USE

[75] Inventors: Johannes Michael Hermann Salbaum, Waldkirchen, Germany; Colin Louis Masters, Darlington, Australia; Konrad Traugott Beyreuter, Heidelberg, Germany

[73] Assignee: Bayer Aktiegsesellschaft, Leverkusen, Germany

[21] Appl. No.: 483,488

[22] Filed: Jun. 7, 1995

Related U.S. Application Data

[63] Continuation of Ser. No. 325,745, Oct. 19, 1994, abandoned, which is a continuation of Ser. No. 153,546, Nov. 16, 1993, abandoned, which is a continuation of Ser. No. 901,330, Jun. 19, 1992, abandoned, which is a division of Ser. No. 393,360, Aug. 14, 1989, Pat. No. 5,151,508, which is a continuation-in-part of Ser. No. 385,758, Jul. 26, 1989, abandoned.

[30] Foreign Application Priority Data

Aug. 30, 1988 [GB] United Kingdom .................. 8820450

[51] Int. Cl.$^6$ ............................... C12Q 1/68; C12P 21/00
[52] U.S. Cl. ................................. 435/6; 435/69.1
[58] Field of Search .............................. 435/172.3, 240.2, 435/320.1, 6, 69.1; 536/24.1, 23.1, 23.2; 935/23, 24, 27, 66, 70, 71

[56] References Cited

PUBLICATIONS

Schorderet (1995) Alzheimer's disease: fundamental and therapeutic aspects. Experientia 51:99–105, Feb. 1995.

*Primary Examiner*—George C. Elliott
*Assistant Examiner*—Robert Schwartzman
*Attorney, Agent, or Firm*—Sprung Kramer Schaefer & Briscoe

[57] ABSTRACT

The present invention is related to the promoter of the gene for the human precursor of the Alzheimer's Disease A4 amyloid protein (PAD gene). Another object of the present invention is the use of this promoter in a method of establishing a screening model for the Alzheimer's Disease. Thus, the present invention is also related to a vector useful in the transfection of cells and the cells and animals transfected therewith.

2 Claims, 4 Drawing Sheets

```
              10         20         30         40         50
BamHI         .          .          .          .          .
       GGATCCTAA  CCCAATATCT GCTGTCCTTA TAACAAGAGG AGATTAGGGC
       ACAGTAAGAC ACAGAGGGAA GACCATGTGA GAATACAGGG AGAAGGTGGC
       CATCTGCAAG CCAAGGAGAG AGGCCTCAGA AGTAACCAAC TCAGCCAACA
       CCTCGATTTC AGACTTCCAG CCTCCTGAAA TGTGAGGAAA TACATTTCTG
-3500  GTGTTTGATC CATCCAGTCT ATGGTAAGTT ATGGCACCCT GCAGGGTTCA
       TCTGGCTCAG ACTTAACGAT TGCTTTTGGT GATATTTATA GGGCACAGAT
       AACAGCCTAA ACACAAGACG ACAGAAACGC GGCCCAGCAG ACTATGCATA
       AAATAGAAAT GGGGTATCTG GACCAATTGG AGTCTGCAGT GGGATCCGGT
       TACTAAAACA GTCAAATGCA ACATGAGGCT CCAGGCAGAG TAGTGGGCAA
       CATCTCCCAT GTTGCAGCAG TCAGAGCACA CTTCGAGTAC TGTAAAAAGA
       CACAGACAAG GCAGAACACT TTAGAGAATG GCCAAGGTGT GGAAGGAACG
       AGAAACCATG CCATTATGCA ACTGTTGAAG GAAGTGCCTG TTTTACCTTG
       TGAAGAGAAG ACTCTAGAGG AAGAAGTAGC ATGAAAACAG CTGGCAAATT
       TGTAAAGATC TGAAGTGTGC AAAAGAATTA TTCTGCTTGG TCACTGGGCA
-3000  ATACAAGGAT ATCTGAGTGG GAGTTTAAAG GCGGGGGATG TGAGCTTTAA
       ATGGGATAAG AACATTCTAG TAACCAGAAA TGCCCAAAGA TAGAATGCAC
       AGTCTGGAGA GCCAGTGAAT ATCTCACAAA TGGAGACACT TGAAACTAGG
       ATGGGGATGC TGTTGTAGGA ATTCCAGCAG ACAAGTGGTT GTTGGTTCCT
       TCCCCAACTT TGTAGGGTTA TAACTAGGGA TGTTCCTGCG TTTTCTGCTT
       GGAGGATCTG CAAGACACCT CAGGGCAGGA AATGGCATTA AATGCAGAAC
       AGAGCTAGTG GCTGAAAAGC AAAAAGCCAT CAGGATCTCT GGAGTAGTGA
       AGGAACCAGA GAACATGCAG GCAATGTCCA TCATTCTGAC GCAATCAGCA
       GCGATAATCA TCTTCCCCCA GGAACATCTT GACCAGGGAA TGTGTCAGTG
       TTGGTGAATT TCAACAGTGG AAAGAGAAAC TGCTAAATCT AAGAACTTTA
-2500  ATTTTTATAG GTTATGATCT CATCTCTACA ATTTTGAATT TCATGCTCAA
       TAAAAGTTCC TTACTCTCTT TTTTTTTTTT TGAGACGGAG TCTCGCTCTG
       TCGCCCAGGC TGGAGTGCAG TGGCGCGATC TCGGCTCACT TCAAGCTCAG
       CTCCCGGGTT CACGCCATTC TCCTGCCTCA GCCTCCCAGT AGCTGGGACT
```

FIG. 1A

```
         ACAGCGCCCG CCACGACGCC CGGCTAATTT TTTGTATTTT TAGTAGAGAC
         GGGGTTTCAC CGTGTTAGCC AGGATGGTGT TGATCTCCTG ACCTCGTGAT
         CCGCCCGCCT CAGCCTCCCA AGAAAAGTC  CCTCACTCTT AAAGTTGCCT
         CCTCCTTCCC AGGGCTGGCT TCATGGGCAT CCAACCCTCC AGAGTCTCAC
         AGGCCCTGCG GTGGGAGGAG CCCCATGCTT GGTTTAACGC TCTGCCATTG
         CCATCTTAAA ATTCTTAATT TAATTTTTTT TCTTTTTTTT TGAGGTGGAG
-2000    TCTCGCTCTG TCGCCCAGGC TGGAGTGCAA TGGCACAATC TTGGCTCACT
         GCAACCTCCG CCTCCCAGGT TCAAGCGATT CTCCTGCCTC AGCCTCTGGA
         GTAGCTGGGA TTACAGGCAG GAGTAACCAC GCTCGGCTAA TTTTTGCATT
         TTTAGTAGAC ATGGGGGTTT CACCATGTTG GCCAGGCTGG TCTAGAACTC
         CTGACCTCAG GTGATCTCCC ACCCTGGGCC TCCTAAAGTG CTGGGATTAC
         AGGCATGAGC CACCAGGCCC GGCCTTAAAA TTCTTAATAA TGTAACAAAG
         GGTCTCACGT TTGCATTTTG CAGTGGACTC TGCAAGATTG TAGCTTGGAC
         CACGTTCTCT TGCATTCAGA TACCTTCTTT TTGCCTTATT TGCTCATGCA
         GACCCGGAAC AAATACGGAA TTGCGGTGGT AAATGTGGTG CAGAAAGTGA
         ACAACTGGGT TTGTCCTGTC ACTTTAGGCT TTTCCCTGTG TCCCAGCTTC
-1500    ATGTCACTTA CTTGCTATTA GATTTGGGAG TTCATTAGCT TCATTTTCCT
              10         20         30         40         50

.          .          .          .          .
         GATGTATAAA TAGGAATAAT AGTAACAGCC TCTTTGGCTT TTGTAGGAAG
         TAAATGACAT GAAGCGTATA AACAAATACT GCATGACAAT AAATATTTGT
         CCTTATTTGT TGAGGACATC CAAAGGACAT TCAGGGGCAA AAGTAATCCA
         AGAGTCAAGA CTGAATGCCT AGTGCGGAAA AAGACACACA AGACAACATT
         TAGGGGAGCT GGTACAGAAA TGACTTCCCA GAAGAAGTCT GTACCCCGCT
         GCCTGAGCCA TCCTTCCCGG GCCTCGGCAC CCTTGTCAGC GCAATGAGCA
         AGGGAGAGAA GGCAGCAGTG CAGCCTCAGA AGGGCCAGCG CACTCCCTGG
         CTTCAGTCCT TCGCTCCAAG CCCTGTGTGG AGTGGGCTGT GGCTTGGTAA
         CTAAACGCTA CTTCAGGTCA AGAGCAGGGG ATATATCTGG GCAGTTCTAG
-1000    AGCATTCTAA ACTATCTGGA CACTAACTGG ACAGTGGACG GTTTGTGTTT
         AATCCAGGAG AAAGTGGCAT GGCAGAAGGT TCATTTCTAT AATTCAGGAC
```

FIG. 1B

```
-900  AGACACAATG AAGAACAAGG GCAGCGTTTG AGGTCAGAAG TCCTCATTTA
      CGGGGTCGAA TACGAATGAT CTCTCCTAAT TTTTCCTTCT TCCCCAACTC
-800  AGATGGATGT TACATCCCTG CTTAACAACA AAAAAAGACC CCCCGCCCCG
      CAAAATCCAC ACTGACCACC CCCTTTAACA AAACAAAACC AAAAACAAAC
-700  AAAAATATAA GAAAGAAACA AAACCCAAGC CCAGAACCCT GCTTTCAAGA
      AGAAGTAAAT GGGTTGGCCG CTTCTTTGCC AGGGCCTGCG CCTTGCTCCT
-600  TTGGTTCGTT CTAAAGATAG AAATTCCAGG TTGCTCGTGC CTGCTTTTGA
      CGTTGGGGGT TAAAAAATGA GGTTTTGCTG TCTCAACAAG CAAAGAAAAT
                           HindIII
-500  CCTATTTCCT TTAAGCTTCA CTCGTTCTCA TTCTCTTCCA GAAACGCCTG
      CCCCACCTCT CCAAACCGAG AGAAAAAACG AAATGCGGAT AAAAACGCAC
                                       MspI
-400  CCTAGCAGCA GTCCTTTATA GCACACCCCC GGGAGGCCTG CGGGGTCGGA
      TGATTCAAGC TCACGGGGAC GAGCAGGAGC GCTCTCGACT TTTCTAGAGC
                                          ** ***   *** **
                            *
-300  CTCAGCGTCC TAGGACTCAC CTTTCCCTGA TCCTGCACCG TCCCTCTCCT
      GGCCCCAGAC TCTCCCTCCC ACTGTTCACG AAGCCCAGGT GGCCGTCGGC
       MspI
-200  CGGGGAGCGG AGGGGGCGCG TGGGGTGCAG GCGGCGCCAA GGCGCTGCAC
                                  MspI
      CTGTGGGCGC GGGGCGAGGG CCCCTCCCGG CGCGAGCGGG CGCAGTTCCC
       MspI                                           MspI
-100  CGGCGGCGCC GCTAGGGGTC TCTCTCGGGT GCCGAGCGGG GTGGGCCGGA
-50   TCAGCTGACT CGCCTGGCTC TGAGCCCCGC CGCCGCGCTC GGGCTCCGTC
+1    AGTTTCCTCG GCAGCGGTAG GCGAGAGCAC GCGGAGGAGC GTGCGCGGGG
       MspI
+51   GCCCCGGGAG ACGGCGGCGG TGGCGGCGCG GGCAGAGCAA GGACGCGGCG
      BamHI
+101  GATCC
```

FIG. 1C

PROMOTER OF THE GENE FOR THE HUMAN PRECURSOR OF THE ALZHEIMER'S DISEASE AND ITS USE

CROSS REFERENCE TO RELATED APPLICATION

This is a continuation of application Ser. No. 08/325,745, filed on Oct. 19, 1994, now abandoned, which is a continuation of application Ser. No. 08/153,546, filed on Nov. 16, 1993, now abandoned, which is a continuation of application Ser. No. 07/901,330, filed on Jun. 19, 1992, now abandoned which is a division of application Ser. No. 07/393,360, filed Aug. 14, 1989, now U.S. Pat. No. 5,151,508, which is a continuation-in-part of application Ser. No. 07/385,758, filed Jul. 26, 1989, now abandoned.

The present invention is related to the promoter of the gene for the human precursor of the Alzheimer's Disease A4 amyloid protein (PAD gene).

Another object of the present invention is the use of this promoter in a method of establishing a screening model for the Alzheimer's Disease. Thus the present invention is also related to a vector useful in the transfection of cells and the cells and animals transfected therewith.

The pathological hallmark of Alzheimer's disease (AD) is the deposition of fibrillar aggregates of the 42/43-residue amyloid A4 protein (also termed β-protein) (Glenner and Wong, 1984, Biochem. Biophys. Res. Commun., 122, 885–890). Masters et al., (1985) Poc. Natl. Acad. Sci. USA, 82, 4245–4249, EMBO J., 11, 2757–2763. Protein sequencing of amyloid isolated from brain of patients with AD and aged individuals with Down's syndrome (DS) revealed the presence of the A4 protein in both conditions (Beyreuther et al., (1986) Discussions in Neuroscience, 3, 68–79).

Recently, molecular cloning based on the sequence of the A4 protein indicated that it is encoded as part of a larger precursor (PreA4) that maps to chromosome 21 (Kang et al., (1987) Nature, 325, 733–736; Goldgaber et al., (1987) Science, 235, 877–880; Tanzi et al., (1987) Science, 235, 880–884). Two mRNA-bands (Kang et al., (1987) Nature, 325, 733–736) have now been accounted for by the demonstration of three alternative splicing products of the amyloid gene (Ponte et al. (1988) Nature, 331, 525–527; Tanzi et al., (1988) Nature, 331, 528–530; Kitaguchi et al., (1988) Nature, 331, 530–532). The smallest of these products, the 695-residue precursor protein (PreA4$_{695}$), has been synthesized in vitro and shown to be a N-glycan membrane protein that spans the lipid bilayer once (Dyrke et al., (1988) EMBO J., 7, 949–957). At least two other forms of PreA4 exist (PreA4$_{751}$ and PreA$_{751}$ and PreA4$_{770}$), both containing a 56 residue insert which has a protease-inhibitory function. The amyloidogenic A4 protein is derived in part from the transmembrane domain and from part of the adjacent extracellular N-glycan domain. A precursor-product relationship has been demonstrated. This suggests that membrane damage and proteolytic cleavage could be important events which precede the release of the A4 protein.

The A4 gene is expressed in brain and peripheral tissues, such as muscle and epithelial cells (Goeder, (1987) EMBO J., 6, 3627–3632; Bahmanyar et al., (1987) Science, 237, 77–88; Zimmermann et al., (1988) EMBO J., 7, 367–372; Shivers et al., (1988) EMBO J., 7, in press), yet for reasons still unknown the amyloid deposits in AD are confined to the brain.

Recently, in situ hybridisation analyses were published that indicate an alteration of the amount of PreA4 mRNA in brains of AD patients when compared to normal individuals (Higgins et al., (1988) Proc. Natl. Acad. Sci. USA, 85, 1297–1301) Cohen et al., (1987) Science, 237, 77–88; Lewis et al., (1988) Proc. Natl. Acad. Sci. USA, 85, 1691–169). These results implicate a role for gene regulation in AD.

To express questions about the breakout of that disease, its course and for establishing a drug-screening model it was first deemed to be necessary to isolate the promoter of the amyloid A4 precursor gene.

DESCRIPTION OF THE FIGURES

FIGS. 1A–C is the nucleotide sequence of the 3.8 kb Bam H1 fragment of clone PN-1 which contains the promoter region for the precursor to the human A4 amyloid protein.

MATERIALS AND METHODS

Cloning and DNA Sequencing

Figure 2:
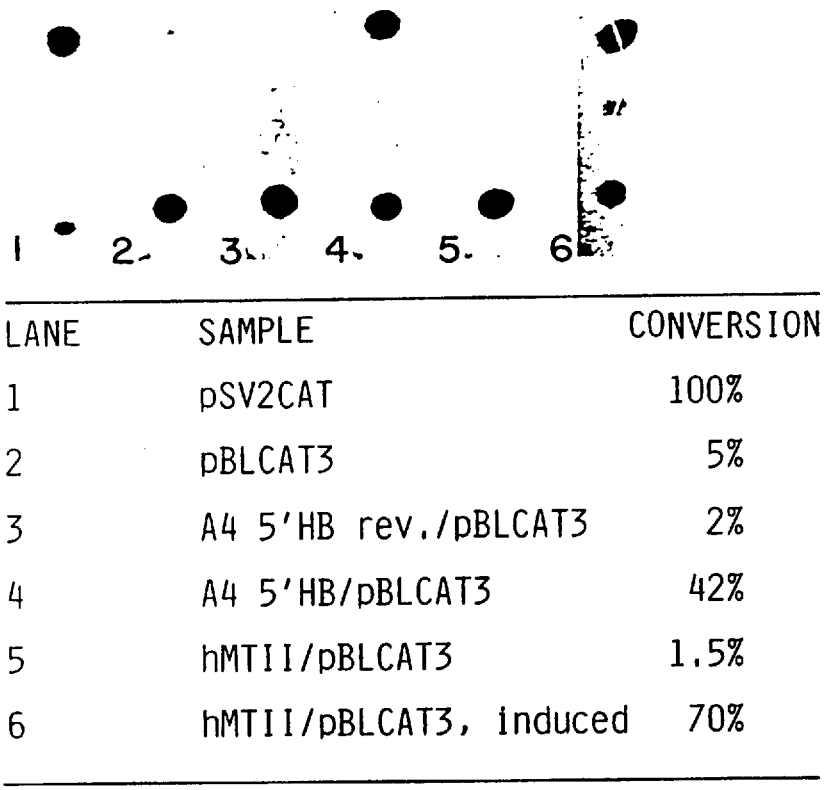
FIG. 2 demonstrates promoter function measured by chloramphenicol acetyltransferase activity. Plasmid constructs where promoters are operatively linked to the CAT gene were transfected into HeLa cells. Lane 1: pSV2CAT; Lane 2: CAT gene without a promoter; Lane 3: promoter region for the precursor to the human A4 amyloid protein in reverse orientation; Lane 4: promoter region for the precursor to the human A4 amyloid protein in correct orientation; Lane 5: human metallothionein promoter.

Clone H,1.30 was isolated from a chromosome 21 library using the BamHI AccI fragment (−47 to +27, Kang et al., (1987) Nature, 325, 733–736) of the PreA4$_{695}$ cDNA as probe. Hybridisations were performed in 5×SSPE, 50% formamide, 1×Denhardt's solution, 1 mM EDTA at 41° C. with 10$^6$ cpm/ml of randomly primed probe (Feinberg and Vogelstein, (1984) Anal. Biochem., 137, 266). A 593 bp HindIII BamHI fragment of clone H1,30 was subcloned into M13 vectors and sequenced on both strands. This fragment also was used to screen a human genomic library and to isolate clone PN.1. A 3.8 kb BamHI fragment was subcloned into a Bluescipt vector (pKS+, Genofit, Heidelberg). A set of ordered deletions along the DNA was constructed with the help of Exonuclease III and Mung Bean Nuclease (Genofit, Heidelberg). DNA from 12 deletion plasmids was purified on CaCl gradients and used for DNA sequencing. The chain termination method (Sanger et al. (1977) Proc. Natl. Acad. Sci. USA, 74, 5463–5467) was performed using T7 DNA Polymerase (Sequenase, USB) on single stranded as well as on denatured plasmid DNA templates (Chen and Seeburg, (1985) DNA, 4, 165–170).

Nuclease S1 Protection and Primer Extension Analysis

The Nuclease S1 protection assay was performed as described (Ruppert et al. 1986). A uniformly labelled single stranded DNA probe was synthesised by annealing an oligonucleotide primer 5'-GCCGCGTCCTTGCTCTGC-3' (SEQ ID NO:1) to mha6 template DNA (a M13mp19 clone of the 593 bp HindIII BamHI PAD gene 5' end fragment) and extension with Klenow polymerase (Boehringer Mannheim) to the HindIII site. The probe was hybridised to 10 μg of total human fetal brain RNA, digested with S1 nuclease (Boehringer Mannheim) and the resulting products analysed on a 6% sequencing gel.

For primer extension analysis, the same annealing mix as for the S1 probe was prepared. Extension of the oligonucleotide with Klenow polymerase was performed with dGTP, dTTP and α[P$^{32}$]dCTP in the absence of dATP. The resulting 29 bp labelled primer was purified on a 6% denaturing (8M urea) polyacrylamide gel. 10$^5$ cpm of primer were annealed to 20 μg of total fetal brain RNA for 30 min at 42° C. in 40 mM TrisCl pH 8.3, 80 mM NaCl, 6 mM $MgCl_2$, 2.5 mM DTT. After addition of all four dNTPs at 0.5 mM and 20u AMV reverse transcriptase (Genofit, Heidelberg). The reaction was incubated for 30 minutes at 42° C. After ethanol precipitation, products were separated on a 6% sequencing gel and subjected to autoradiography.

In Vivo Promoter Assay

In order to assay in vivo promoter activity, CAT assays in HeLa cells transfected with the appropriate constructs were performed as described (Schöler and Gruss, (1985) Cell, 36, 403–411). The 593 bp HindIII BamHI fragment was cloned into pBLCAT3 (Luckow and Schütz, (1987) Ac. Res., 15, 5490). To generate a construct with the PAD gene promoter in reverse orientation to the CAT gene, the 593 bp HindIII BamHI fragment was treated with Klenow polymerase and cloned via blunt ends into the HindII site of pUC19. The insert of a properly oriented clone was cut out with HindIII and BamHI and cloned into pBLCAT3, pSV2CAT and the hMTII promoter (Karin et. al., (1984) Nature, 308, 513–519) cloned into pBLCAT3 were used as controls.

Cloning of the PAD Gene Promoter

Genomic clones were isolated from the 5' end of the PAD gene. A BamHI AccI fragment from position −47 to +227 of A4 amyloid precursor cDNA (Kang et al., 1987), which encodes the shortest precursor cDNA (Kang et al., 1987), which encodes the shortest 695 residue product ($PreA4_{695}$) was used to screen a library of flow-sorted human chromosome 21. Clone H1.30 was found to contain a 2.8 kb HindIII fragment which was subcloned into pUC19. The fragment contained a single BamHI site. The 593 bp HindIII BamHI fragment of clone H1.30 was cloned into M13 vectors and the DNA sequence of both strands was determined. This DNA fragment was found to contain 99 bp upstream of the BamHI site which were identical to the reported 5' untranslated cDNA sequence of $PreA4_{695}$, except for one additional G in the genomic DNA at cDNA position −96 to −99. The genomic DNA showed a stretch of five consecutive Gs versus four in the cDNA. The 488 bp upstream of the cDNA sequence were expected to be the promoter region of the PAD gene. In order to obtain a clone which contains more upstream DNA, the 593 bp HindIII BamHI fragment was used as a probe to screen a human genomic library. Clone PN.1 was isolated and found to have 3.8 kb BamHI fragment which hybridised to the probe. This fragment was subcloned and its DNA sequence was determined (FIG. 1). The DNA contains two copies of an Alu-type repetitive sequence in the same orientation at positions −2436 to −2179 and −2020 to −1764.

PAD Promoter Elements

The DNA sequence upstream of the multiple RNA 5'termini (FIG. 1) does not contain a typical TATA box and has a high GC content. Between positions −1 and −400 the DNA is comprised of 72% GC. The ratio of the dinucleotide CpG, the target site for DNA methylation, versus GpC is about 1:1 around the RNA start site. At position −45 as well as −350, relative to the strongest 5'end signal, a heptamer sequences were found which are in good agreement to the binding consensus sequence of the transcription factor AP-1 (TGACTCA, Lee et al., (1987) Nature, 325, 368–372). The sequence starting at position −317 corresponds very well to the heat shock control element (HSE), whose consensus sequence is CT-GAA-TTC-AG (Wu et al., (1987) Science, 238, 1247–1253). Furthermore, six copies of a GC-rich element following a consensus of $GGGCGC_A{}^GGG$ can be located between positions −198 and −105. The features of multiple RNA start sites, the absence of a typical TATA box, the high GC content of the DNA upstream of the RNA starts, and the presence of a GC-rich box places the promoter of the PAD gene in the class of promoters of "housekeeping" genes, like the adenosine deaminase gene (Valerio et al., (1985) EMBO J., 4, 437–443) or the gene for dihydrofolate reductase (Crouse et al., (1982) J. Biol. Chem., 257, 1357–1370). The promoter of the hamster PrP gene, the product of which gives rise to brain amyloid deposits in scrapie infected animals, is organised in a similar fashion (Basler et al., (1986) Cell, 46, 417–428).

Promoter Activity in Vivo

The 593 bp HindIII BamHI fragment was tested for its ability to show promoter activity in vivo. It was cloned into pBLCAT3 (Luckow and Schütz, (1987) Ac. Res., 15, 5490) in correct as well as in reverse orientation to the chloramphenicol acetyltransferase (CAT) gene. These constructs were transfected into HeLa cells and CAT activity was measured (FIG. 2). The SV40 promoter of pSV2CAT served as high control (lane 1), resulting in a complete conversion of chloramphenicol into its acetylated derivatives. Transfection with the PAD promoter in reverse orientation yielded 2% conversion (lane 3), comparable to the CAT vector without an inserted promoter (5%, lane 2) or the non-induced human metallolithionine II (hmtII) promoter (1.5%, lane 5). When induced with 2 mM $Zn^{2+}$, the hmtII promoter produced 70% conversion in oun assay conditions. The PAD promoter fragment in correct orientation gave 42% conversion (FIG. 2, lane 4). This result clearly shows that the 593 bp genomic fragment can function as a promoter in an in vivo assay. Together with the results of the 5'end mapping of the $PreA4_{695}$ mRNA we conclude that indeed the promoter of the PAD gene has been isolated from the genomic clones.

In the same manner as the CAT gene the human precursor of Alzheimer's Disease A4 amyloid protein of German Patent Application P 3 702 789.1 can be used as reporter gene.

The method of preparing transgenic animals is described in Hogan, B., et al., in Manipulating the Mouse Embryo, A Laboratory Mannual, Cold Spring Harbor Laboratory, 1986.

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (x i) SEQUENCE DESCRIPTION: SEQ ID NO:1:

| GCCGCGTCCT TGCTCTGC | 18 |

(2) INFORMATION FOR SEQ ID NO: 2:

(i) SEQUENCE CHARACTERISTICS:
(A) LENGTH: 7 base pairs
(B) TYPE: nucleic acid
(C) STRANDEDNESS: single
(D) TOPOLOGY: linear (x i) SEQUENCE DESCRIPTION: SEQ ID NO:2:

| TGACTCA | 7 |

(2) INFORMATION FOR SEQ ID NO: 3:

(i) SEQUENCE CHARACTERISTICS:
(A) LENGTH: 14 base pairs
(B) TYPE: nucleic acid
(C) STRANDEDNESS: single
(D) TOPOLOGY: linear (x i) SEQUENCE DESCRIPTION: SEQ ID NO:3:

| GTNGAANNTT CNAG | 14 |

(2) INFORMATION FOR SEQ ID NO: 4:

(i) SEQUENCE CHARACTERISTICS:
(A) LENGTH: 9 base pairs
(B) TYPE: nucleic acid
(C) STRANDEDNESS: single
(D) TOPOLOGY: linear (x i) SEQUENCE DESCRIPTION: SEQ ID NO:4:

| GGGCGCRGG | 9 |

(2) INFORMATION FOR SEQ ID NO: 5:

(i) SEQUENCE CHARACTERISTICS:
(A) LENGTH: 3804 base pairs
(B) TYPE: nucleic acid
(C) STRANDEDNESS: single
(D) TOPOLOGY: linear (x i) SEQUENCE DESCRIPTION: SEQ ID NO:5:

| GGATCCTAAC CCAATATCTG CTGTCCTTAT AACAAGAGGA | 40 |
| GATTAGGGCA CAGTAAGACA CAGAGGGAAG ACCATGTGAG | 80 |
| AATACAGGGA GAAGGTGGCC ATCTGCAAGC CAAGGAGAGA | 120 |
| GGCCTCAGAA GTAACCAACT CAGCCAACAC CTCGATTTCA | 160 |
| GACTTCCAGC CTCCTGAAAT GTGAGGAAAT ACATTTCTGG | 200 |
| TGTTTGATCC ATCCAGTCTA TGGTAAGTTA TGGCACCCTG | 240 |
| CAGGGTTCAT CTGGCTCAGA CTTAACGATT GCTTTTGGTG | 280 |
| ATATTTATAG GGCACAGATA ACAGCCTAAA CACAAGACGA | 320 |
| CAGAAACGCG GCCCAGCAGA CTATGCATAA AATAGAAATG | 360 |
| GGGTATCTGG ACCAATTGGA GTCTGCAGTG GGATCCGGTT | 400 |
| ACTAAAACAG TCAAATGCAA CATGAGGCTC CAGGCAGAGT | 440 |
| AGTGGGCAAC ATCTCCCATG TTGCAGCAGT CAGAGCACAC | 480 |

```
TTCGAGTACT   GTAAAAAGAC   ACAGACAAGG   CAGAACACTT                520
TAGAGAATGG   CCAAGGTGTG   GAAGGAACGA   GAAACCATGC                560
CATTATGCAA   CTGTTGAAGG   AAGTGCCTGT   TTTACCTTGT                600
GAAGAGAAGA   CTCTAGAGGA   AGAAGTAGCA   TGAAAACAGC                640
TGGCAAATTT   GTAAAGATCT   GAAGTGTGCA   AAAGAATTAT                680
TCTGCTTGGT   CACTGGGCAA   TACAAGGATA   TCTGAGTGGG                720
AGTTTAAAGG   CGGGGGATGT   GAGCTTTAAA   TGGGATAAGA                760
ACATTCTAGT   AACCAGAAAT   GCCCAAAGAT   AGAATGCACA                800
GTCTGGAGAG   CCAGTGAATA   TCTCACAAAT   GGAGACACTT                840
GAAACTAGGA   TGGGGATGCT   GTTGTAGGAA   TTCCAGCAGA                880
CAAGTGGTTG   TTGGTTCCTT   CCCCAACTTT   GTAGGGTTAT                920
AACTAGGGAT   GTTCCTGCGT   TTTCTGCTTG   GAGGATCTGC                960
AAGACACCTC   AGGGCAGGAA   ATGGCATTAA   ATGCAGAACA               1000
GAGCTAGTGG   CTGAAAAGCA   AAAAGCCATC   AGGATCTCTG               1040
GAGTAGTGAA   GGAACCAGAG   AACATGCAGG   CAATGTCCAT               1080
CATTCTGACG   CAATCAGCAG   CGATAATCAT   CTTCCCCCAG               1120
GAACATCTTG   ACCAGGGAAT   GTGTCAGTGT   TGGTGAATTT               1160
CAACAGTGGA   AAGAGAAACT   GCTAAATCTA   AGAACTTTAA               1200
TTTTTATAGG   TTATGATCTC   ATCTCTACAA   TTTTGAATTT               1240
CATGCTCAAT   AAAAGTTCCT   TACTCTCTTT   TTTTTTTTT                1280
GAGACGGAGT   CTCGCTCTGT   CGCCCAGGCT   GGAGTGCAGT               1320
GGCGCGATCT   CGGCTCACTT   CAAGCTCAGC   TCCCGGGTTC               1360
ACGCCATTCT   CCTGCCTCAG   CCTCCCAGTA   GCTGGGACTA               1400
CAGCGCCCGC   CACGACGCCC   GGCTAATTTT   TTGTATTTTT               1440
AGTAGAGACG   GGGTTTCACC   GTGTTAGCCA   GGATGGTGTT               1480
GATCTCCTGA   CCTCGTGATC   CGCCCGCCTC   AGCCTCCCAA               1520
AGAAAGTCC    CTCACTCTTA   AAGTTGCCTC   CTCCTTCCCA               1560
GGGCTGGCTT   CATGGGCATC   CAACCCTCCA   GAGTCTCACA               1600
GGCCCTGCGG   TGGGAGGAGC   CCCATGCTTG   GTTTAACGCT               1640
CTGCCATTGC   CATCTTAAAA   TTCTTAATTT   AATTTTTTTT               1680
CTTTTTTTTT   GAGGTGGAGT   CTCGCTCTGT   CGCCCAGGCT               1720
GGAGTGCAAT   GGCACAATCT   TGGCTCACTG   CAACCTCCGC               1760
CTCCCAGGTT   CAAGCGATTC   TCCTGCCTCA   GCCTCTGGAG               1800
TAGCTGGGAT   TACAGGCAGG   AGTAACCACG   CTCGGCTAAT               1840
TTTTGCATTT   TTAGTAGACA   TGGGGGTTTC   ACCATGTTGG               1880
CCAGGCTGGT   CTAGAACTCC   TGACCTCAGG   TGATCTCCCA               1920
CCCTGGGCCT   CCTAAAGTGC   TGGGATTACA   GGCATGAGCC               1960
ACCAGGCCCG   GCCTTAAAAT   TCTTAATAAT   GTAACAAGG                2000
GTCTCACGTT   TGCATTTTGC   AGTGGACTCT   GCAAGATTGT               2040
AGCTTGGACC   ACGTTCTCTT   GCATTCAGAT   ACCTTCTTTT               2080
```

| | | | | |
|---|---|---|---|---|
| TGCCTTATTT | GCTCATGCAG | ACCCGGAACA | AATACGGAAT | 2120 |
| TGCGGTGGTA | AATGTGGTGC | AGAAAGTGAA | CAACTGGGTT | 2160 |
| TGTCCTGTCA | CTTTAGGCTT | TTCCCTGTGT | CCCAGCTTCA | 2200 |
| TGTCACTTAC | TTGCTATTAG | ATTTGGGAGT | TCATTAGCTT | 2240 |
| CATTTTCCTG | ATGTATAAAT | AGGAATAATA | GTAACAGCCT | 2280 |
| CTTTGGCTTT | TGTAGGAAGT | AAATGACATG | AAGCGTATAA | 2320 |
| ACAAATACTG | CATGACAATA | AATATTTGTC | CTTATTTGTT | 2360 |
| GAGGACATCC | AAAGGACATT | CAGGGGCAAA | AGTAATCCAA | 2400 |
| GAGTCAAGAC | TGAATGCCTA | GTGCGGAAAA | AGACACACAA | 2440 |
| GACAACATTT | AGGGGAGCTG | GTACAGAAAT | GACTTCCCAG | 2480 |
| AAGAAGTCTG | TACCCCGCTG | CCTGAGCCAT | CCTTCCCGGG | 2520 |
| CCTCGGCACC | CTTGTCAGCG | CAATGAGCAA | GGGAGAGAAG | 2560 |
| GCAGCAGTGC | AGCCTCAGAA | GGGCCAGCGC | ACTCCTGGC | 2600 |
| TTCAGTCCTT | CGCTCCAAGC | CCTGTGTGGA | CTGGGCTGTG | 2640 |
| GCTTGGTAAC | TAAACGCTAC | TTCAGGTCAA | GAGCAGGGA | 2680 |
| TATATCTGGG | CAGTTCTAGA | GCATTCTAAA | CTATCTGGAC | 2720 |
| ACTAACTGGA | CAGTGGACGG | TTTGTGTTTA | ATCCAGGAGA | 2760 |
| AAGTGGCATG | GCAGAAGGTT | CATTTCTATA | ATTCAGGACA | 2800 |
| GACACAATGA | AGAACAAGGG | CAGCGTTTGA | GGTCAGAAGT | 2840 |
| CCTCATTTAC | GGGGTCGAAT | ACGAATGATC | TCTCCTAATT | 2880 |
| TTTCCTTCTT | CCCCAACTCA | GATGGATGTT | ACATCCCTGC | 2920 |
| TTAACAACAA | AAAAAGACCC | CCCGCCCCGC | AAAATCCACA | 2960 |
| CTGACCACCC | CCTTTAACAA | AACAAAACCA | AAAACAAACA | 3000 |
| AAAATATAAG | AAAGAAACAA | AACCCAAGCC | CAGAACCCTG | 3040 |
| CTTTCAAGAA | GAAGTAAATG | GGTTGGCCGC | TTCTTTGCCA | 3080 |
| GGGCCTGCGC | CTTGCTCCTT | TGGTTCGTTC | TAAAGAGAGA | 3120 |
| AATTCCAGGT | TGCTCGTGCC | TGCTTTTGAC | GTTGGGGGTT | 3160 |
| AAAAAATGAG | GTTTTGCTGT | CTCAACAAGC | AAAGAAAATC | 3200 |
| CTATTTCCTT | TAAGCTTCAC | TCGTTCTCAT | TCTCTTCCAG | 3240 |
| AAACGCCTGC | CCCACCTCTC | CAAACCGAGA | GAAAAAACGA | 3280 |
| AATGCGGATA | AAAACGCACC | CTAGCAGCAG | TCCTTTATAG | 3320 |
| CACACCCCCG | GGAGGCCTGC | GGGGTCGGAT | GATTCAAGCT | 3360 |
| CACGGGACG | AGCAGGAGCG | CTCTCGACTT | TTCTAGAGCC | 3400 |
| TCAGCGTCCT | AGGACTCACC | TTTCCCTGAT | CCTGCACCGT | 3440 |
| CCCTCTCCTG | GCCCCAGACT | CTCCCTCCCA | CTGTTCACGA | 3480 |
| AGCCCAGGTG | GCCGTCGGCC | GGGGAGCGGA | GGGGGCGCGT | 3520 |
| GGGGTGCAGG | CGGCGCCAAG | GCGCTGCACC | TGTGGGCGCG | 3560 |
| GGGCGAGGGC | CCCTCCCGGC | GCGAGCGGGC | GCAGTTCCCC | 3600 |
| GGCGGCGCCG | CTAGGGGTCT | CTCTCGGGTG | CCGAGCGGGG | 3640 |
| TGGGCCGGAT | CAGCTGACTC | GCCTGGCTCT | GAGCCCCGCC | 3680 |

-continued

| | | | | |
|---|---|---|---|---|
| GCCGCGCTCG | GGCTCCGTCA | GTTTCCTCGG | CAGCGGTAGG | 3720 |
| CGAGAGCACG | CGGAGGAGCG | TGCGCGGGGG | CCCCGGGAGA | 3760 |
| CGGCGGCGGT | GGCGGCGCGG | GCAGAGCAAG | GACGCGGCGG | 3800 |
| ATCC | | | | 3804 |

We claim:

1. A method for screening for a drug that regulates gene expression from the promoter of the gene for the human precursor of Alzheimer's Disease A4 amyloid protein comprising the steps of:

(a) providing a vector comprising said promoter operably linked to a DNA sequence encoding a reporter protein, (b) transfecting a host cell line with the vector of step (a), (c) exposing the transfected host cell line to a drug, and (d) measuring the expression of the reporter gene, whereby a change in the expression of the reporter protein identifies a drug that regulates expression from the promoter of the gene for the human precursor of Alzheimer's Disease A4 amyloid protein.

2. The method according to claim 1, wherein said DNA sequence encoding a reporter protein encodes for the human precursor of Alzheimer's Disease A4 amyloid protein or the chloramphenicol acetyltransferase protein.

* * * * *